United States Patent
Fukushima et al.

(10) Patent No.: US 7,407,628 B2
(45) Date of Patent: Aug. 5, 2008

(54) BIOSENSOR AND METHOD OF MANUFACTURING BIOSENSOR

(75) Inventors: Hitoshi Fukushima, Tsukuba (JP); Takayuki Kondo, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 841 days.

(21) Appl. No.: 10/911,627

(22) Filed: Aug. 5, 2004

(65) Prior Publication Data

US 2005/0063870 A1    Mar. 24, 2005

(30) Foreign Application Priority Data

Sep. 1, 2003    (JP) ............................. 2003-309285

(51) Int. Cl.
*G01N 21/00* (2006.01)
*G01N 33/53* (2006.01)

(52) U.S. Cl. ................... 422/82.05; 422/82.11; 422/55; 435/6; 435/7.1

(58) Field of Classification Search ........................ None
See application file for complete search history.

(56) References Cited

U.S. PATENT DOCUMENTS

| | | | |
|---|---|---|---|
| 4,755,667 A | 7/1988 | Marsoner et al. | |
| 5,039,490 A | 8/1991 | Marsoner et al. | |
| 5,439,647 A | 8/1995 | Saini | |
| 5,445,934 A | 8/1995 | Fodor et al. | |
| 5,779,978 A | 7/1998 | Hartmann et al. | |
| 5,872,623 A | 2/1999 | Stabile et al. | |
| 6,045,756 A * | 4/2000 | Carr et al. ................. | 422/82.11 |
| 6,084,683 A | 7/2000 | Bruno et al. | |
| 6,197,503 B1 * | 3/2001 | Vo-Dinh et al. ................ | 435/6 |
| 6,469,785 B1 | 10/2002 | Duveneck et al. | |
| 2001/0040679 A1 | 11/2001 | Kawabata et al. | |

FOREIGN PATENT DOCUMENTS

| | | |
|---|---|---|
| EP | 0 797 091 A1 | 9/1997 |
| JP | A 10-125929 | 5/1998 |
| JP | A 10-125930 | 5/1998 |
| JP | A 10-125931 | 5/1998 |
| JP | A 11-344437 | 12/1999 |
| JP | A 2001-296172 | 10/2001 |
| JP | A 2002-9379 | 1/2002 |
| JP | A 2003-156504 | 5/2003 |
| JP | A 2003-185569 | 7/2003 |

* cited by examiner

*Primary Examiner*—Jill Warden
*Assistant Examiner*—Neil Turk
(74) *Attorney, Agent, or Firm*—Oliff & Berridge, PLC

(57) ABSTRACT

Aspects of the invention can be an inexpensive biosensor capable of measuring a number of samples in a short time, and suitable for only one-time use (expendable). The biosensor according to the invention can include a light transmissive substrate, a probe fixing region provided on one face of the light transmissive substrate, a light emitting element provided on the other face of the substrate that irradiates the probe fixing region from the back side thereof, and a light receiving element provided on the other face of the substrate that detects the light intensity of the reflected light from the back side of the probe fixing region. Thereby, a biosensor formed in one substrate can be obtained.

1 Claim, 8 Drawing Sheets

FIG. 13A STEP1

110
20 AlAs layer
10 GaAs substrate

FIG. 13B STEP2

30 Inter transfer film
110
10

FIG. 13C STEP3

30
Lift off  110
10

FIG. 13D STEP4

30
103  110
101 Glass, Si, etc.

FIG. 13E STEP5

40
101

FIG. 13F STEP6

30
110
101

BIOSENSOR AND METHOD OF MANUFACTURING BIOSENSOR

BACKGROUND OF THE INVENTION

1. Field of Invention

Aspects of the invention relate to a biosensor for detecting a biological sample or the like, and in particularly to miniaturization of the biosensor.

2. Description of Related Art

Related biosensors that recognize a detecting object, such as DNA, proteins, and antibody molecules efficiently and correctly in a short time, and extracts information, such as the structure, function, weight, and electric characteristics of the detecting object sample, are important since the human genome analysis has been completed. Related biosensors can include, for example, a method (see, for example, U.S. Pat. No. 5,445,934) of measuring DNA hybridization reaction by the fluorescence intensity, and a method (see, for example, Japanese Unexamined Patent Publication No. 2001-296172) of measuring DNA hybridization reaction by surface plasmon resonance (SPR). When detecting by these optical methods, the measurement result can be obtained relatively promptly. Moreover, related methods (electrophoresis) of measuring differences in the amount of DNA displacement that varies depending on the applied electric-field or the like are used. In this case, the detection can be made with relatively simple equipment.

SUMMARY OF THE INVENTION

However, in these two methods of carrying out the optical measurement, the measurement device thereof is on a large scale and the measurement cost is high. The latter electrophoresis method takes time to obtain the measurement result, and is not suitable for inspecting a number of samples. Therefore, the aspects of invention are intended to provide an inexpensive biosensor which can measure a number of samples in a short time, and is also suitable for only one-time use (expendable). The invention is also intended to provide a method of manufacturing such biosensor.

An exemplary biosensor according to the invention, can include a light transmissive substrate, a probe fixing region provided on one face of the light transmissive substrate, and a light emitting element provided on the other face of the light transmissive substrate that irradiates the probe fixing region from the back side thereof. Here, the light emitting element may include not only a unit element but also a circuit relevant to the light emitting function.

By making such a structure, a biosensor substrate having the probe fixing region and the light emitting element on one substrate can be obtained. On this substrate, hybridization can be carried out by spotting (dropping) a sample. In the probe fixing region of the substrate, a probe (pieces of DNA or the like) with a related structure that uniquely acts to a biological sample is fixed, and the biological sample having a complementary structure is bound by hybridization. Provision may be made to add fluorochrome to this biological sample in advance, or insert fluorochrome as an intercalator in a double helix structure portion made by the binding. The light emitting element directly formed in the substrate is made to emit light, and the fluorochrome accompanying the biological sample that binds to the probe is made to generate fluorescence. The presence of the biological sample can be distinguished by observing this from the outside. The integration of the substrate and the light source simplifies the measurement device. In addition, the sample spotting can be carried out automatically by a drop-discharging device to which an ink-jet technology is applied.

Moreover, an exemplary biosensor according to the invention can include a light transmissive substrate, a probe fixing region provided on one face of the light transmissive substrate, and a light receiving element provided on the other face of the light transmissive substrate that detects the light intensity on the light transmissive substrate side of the probe fixing region. Here, the light receiving element may include not only a unit element but also a circuit relevant to the light receiving function.

By making such a structure, a biosensor substrate having the probe fixing region and the light receiving element on one substrate where the sample spotting is carried out is obtained. A probe (pieces of DNA or the like) with a known structure that uniquely acts to the biological sample is fixed to the probe fixing region in the substrate, and a biological sample having a complementary structure is bound by hybridization. Fluorochrome is added to this biological sample in advance. Alternatively, fluorochrome as an intercalator is inserted in the binding portion. Light is applied to the substrate from the outside to have the biological sample that binds to the probe generate fluorescence. The presence of the biological sample can be distinguished by observing this with the light receiving element directly formed in the substrate. The integration of the substrate and the light receiving element (scanner) simplifies the measurement device.

Moreover, an exemplary biosensor according to the invention can include a light transmissive substrate, a probe fixing region provided on one face of the light transmissive substrate, a light emitting element provided on the other face of the light transmissive substrate that irradiates the probe fixing region from the light transmissive substrate side, and a light receiving element provided on the other face of the light transmissive substrate that detects the light intensity of the reflected light from the light transmissive substrate side of the probe fixing region. Here, the light emitting element and the light receiving element may include not only the unit element, but also a circuit relevant to the light emitting function and the light receiving function.

By making such a structure, a biosensor substrate having the probe fixing region, the light emitting element, and the light receiving element on one substrate where the sample spotting is carried out can be obtained. A probe (pieces of DNA or the like) with a known structure that uniquely acts to the biological sample is fixed to the probe fixing region in the substrate, and the biological sample having a complementary structure can be bound by hybridization. Fluorochrome is added to this biological sample in advance. Alternatively, the fluorochrome as an intercalator is inserted in the bound portion. Light is applied to the biological sample by the light emitting element provided on the substrate to have the biological sample bound to the probe generate fluorescence. The presence of the biological sample can be distinguished by detecting this fluorescence by the light receiving element formed in the substrate. The integration of the substrate in which the sample is arranged, the light emitting element, and the light receiving element (scanner) simplifies the measurement device.

Moreover, such a structure enables the formation of the biosensor which carries out the detection of the biological sample using a surface plasmon resonance (SPR) method.

Another exemplary biosensor according to the invention can include a light transmissive substrate, a plurality of probe fixing regions provided on one face of the light transmissive substrate, a light shielding region formed in the light transmissive substrate that shields the light between the adjacent probe fixing regions, a light emitting element that irradiates the probe fixing region from the light transmissive substrate side, and a light receiving element that detects the light intensity of the reflected light from the light transmissive substrate side of the probe fixing region, the light emitting element and the light receiving element being provided in each probe fixing region on the other face of the light transmissive substrate.

By making such a structure, the biosensor substrate having a plurality of biosensors, a unit of which is a set of the probe fixing region, the light emitting element, and the light receiving element on one substrate, is obtained. A probe (pieces of DNA or the like) with a known structure that uniquely acts to the biological sample is fixed to each probe fixing region in the substrate, and the biological sample having a complementary structure is bound by hybridization.

Fluorochrome is added to this biological sample in advance. Alternatively, fluorochrome as an intercalator is inserted in the bound portion. Light is applied to the biological sample, which is spotted to the probe fixing region by the light emitting element provided in each unit region in the substrate, to have the biological sample bound to the probe generate fluorescence. The presence of the biological sample in each unit region can be distinguished by detecting this fluorescence by the light receiving element provided in each unit region. The integration of the substrate in which the sample is arranged, the light emitting element, and the light receiving element (scanner) simplifies the measurement device. Moreover, the leakage light from the light emitting element (light source) in the adjacent regions is suppressed by light-shielding each unit region, and the influence (noise) on the light receiving element is reduced.

In addition, in cases that the light emitting element in each unit region is made to emit simultaneously, that each light emitting element is made to emit alternately, that an arbitrary light emitting element is made to emit independently, or the like, the measurement of the sample can be carried out with light emitting patterns in various arrays. Thereby, serious consideration can be given to the prevention of the influence of the light leakage from other regions, or a higher priority can be given to the reduction of the measurement time. Moreover, such a structure can also enable the formation of the biosensor which carries out the detection of the biological sample using the surface plasmon resonance (SPR) method.

Preferably, the above-described light transmissive substrate is formed bonding a first substrate in which the probe fixing region is formed, and a second substrate in which at least either one of the light emitting element and the light receiving element is formed. Accordingly, the substrate (first substrate), in which the probe is formed, is prevented as much as possible from being exposed to the semiconductor manufacturing process, like the second substrate in which the light emitting element and the light receiving element are formed and thus contamination of the substrate by chemical substances or the like is prevented. Moreover, shortening the manufacturing time and improving the performance and the reliability can be attained by carrying out the manufacturing process for each substrate in parallel and by optimizing each manufacturing process and each process condition.

Moreover, the light transmissive substrate can be constituted depositing a first substrate in which the probe fixing region is formed, and a second substrate in which the light receiving element is formed, through a filter layer which transmits light with a specific wavelength. In this case, the filter layer extracts the fluorescence of the sample, which then can be detected by the light receiving element.

The probe fixing region in the light transmissive substrate can be set on a microlens or a microprism formed in the light transmissive substrate. The outgoing light of the light emitting element is derived to the back side of the probe fixing region by the microlens or the microprism formed under the probe fixing region in the light transmissive substrate. Moreover, the reflected light from the probe fixing region in the light transmissive substrate is derived to the light receiving element arranged on the other face of the light transmissive substrate through the microlens or the microprism formed in the light transmissive substrate. Such a structure is suitable for forming the biosensor which carries out the detection of the biological sample using the surface plasmon resonance (SPR) method.

Preferably, the light emitting element or the light receiving element is formed by a thin film circuit. By forming the light emitting circuit and the light receiving circuit by a thin film circuit, the outline of the biosensor can be formed in approximately the shape of the substrate on which the sample is mounted. Moreover, the semiconductor thin film circuit of the light emitting element and the light receiving element formed separately in a heat-resistant substrate may be manufactured by transferring to the probe substrate with the technologies of the transfer of a compound semiconductor chip between substrates by epitaxial lift-off process (ELO), and the peel-transfer technology of a semiconductor thin film circuit, as disclosed in Japanese Unexamined Patent Application No. Hei. 10-125929, Japanese Unexamined Patent Application No. Hei. 10-125930, and Japanese Unexamined Patent Application No. Hei. 10-125931. Thereby, a semiconductor thin film circuit with excellent performance can be formed in the biosensor substrate. Moreover, the biosensor can be provided at a lower price by mass-production, and a contamination-free and only one-time use type biosensor can be provided.

As for the light emitting element, for example, a light emitting diode, a vertical-cavity surface-emitting laser, an organic EL element, or the like can be used. Moreover, as for the light receiving element, for example, a photo-diode, a photo-transistor, CCD, or the like can be used.

The probe that uniquely acts to a specific biological sample is fixed to the probe fixing region. The biological sample includes, for example, DNA, proteins, and antibodies. The biosensor substrate to which the probes are fixed in advance may be provided to a client, or a desired probe may be fixed to the biosensor substrate by a client.

Lyophilic processing can be carried out to the probe fixing region in the light transmissive substrate, and liquid repellent processing is carried out to the other regions. Accordingly, the distribution accuracy in spotting samples and in drop-discharging will be improved.

A metal thin film is formed in the probe fixing region in the light transmissive substrate. For example, gold is used. Use of gold, as a base, facilitates pieces of DNA to be fixed to the probe fixing region, and furthermore, allows surface plasmon resonance measurement.

An exemplary biosensor according to the invention can be constituted by sequentially arranging in one direction a substrate, in which a thin film light emitting element is formed on one face, a light transmissive substrate in which a probe fixing region is formed on one face, a substrate where a thin film filter that transmits light with a specific wavelength is formed, and a substrate, in which a thin film light receiving element is formed on one face. By making such a structure, a biosensor can be constituted by stacking the substrates in which thin film elements are formed.

A biosensor according to the invention can be constituted by sequentially arranging in one direction a substrate, in which a plurality of thin film light emitting elements are arranged on one face, a light transmissive substrate, in which a plurality of probe fixing regions are arranged corresponding to the plurality of thin film light emitting elements on one face, a substrate in which a thin film filter that transmits light with a specific wavelength is formed, a substrate, in which a plurality of thin film light receiving elements are arranged corresponding to the plurality of probe fixing regions on one face.

By making such a structure, the biosensors of an array can be constituted by stacking the substrates in which the thin film elements are formed.

A method of manufacturing a biosensor according to the invention can include forming a probe fixing region on a part of or the whole of one face of a light transmissive substrate by carrying out lyophilic processing or forming a metal thin film, and transferring at least either one of a light emitting element chip and a light receiving element chip to the other face of the substrate, corresponding to the probe fixing region. By making such a structure, a biosensor can be formed in one substrate.

An exemplary method of manufacturing a biosensor according to the invention can include forming a probe fixing region on one face of a light transmissive first substrate, transferring at least either one of a light emitting element chip and a light receiving element chip on one face of a second substrate corresponding to the probe fixing region, and bonding the first and the second substrates. By making such a structure, a biosensor can be formed bonding two substrates.

Preferably, the probe is formed in the probe fixing region after carrying out the formation of the substrate. Accordingly, probe contamination and probe damage during the manufacturing process can be reduced or prevented as much as possible.

According to the invention, a probe, a light emitting element, a light receiving element, a microlens, or the like, can be collected as many as possible, on one substrate or a combined substrate, therefore, a small and inexpensive biosensor can be obtained.

BRIEF DESCRIPTION OF THE DRAWINGS

The invention will be described with reference to the accompanying drawings, wherein like numerals reference like elements, and wherein:

FIG. 13 is a process flowchart explaining the process of transferring a compound semiconductor device to a glass substrate using epitaxial lift-off process (ELO);

DETAILED DESCRIPTION OF PREFERRED EMBODIMENTS

Figure 1:
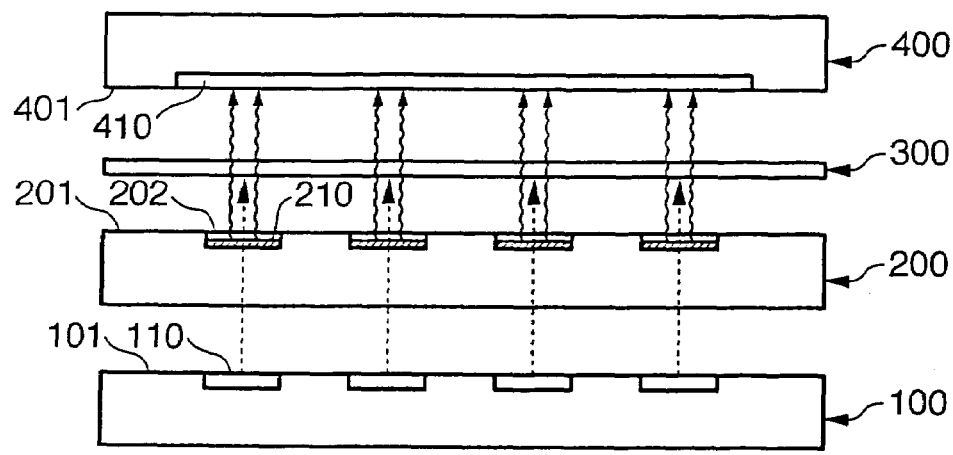
FIG. 1 is an explanatory view explaining a biosensor that is constituted forming a thin film device in a substrate according to an embodiment of the invention.

Hereinafter, exemplary embodiments of the invention will be described with reference to the drawings. FIG. 1 shows a basic structure of the invention, where each element of a biosensor is formed by a substrate or a thin film, and each substrate is arranged in one direction. In this figure, the biosensor includes a light emitting element substrate 100, a probe substrate 200, an optical filter 300, and a light receiving element substrate 400.

The light emitting element substrate 100 can be formed by arranging a plurality of light emitting elements 110, such as vertical-cavity surface-emitting laser (VCSEL), light emitting diode (LED), and an organic EL, on one face (upper face) of an insulating substrate 101. The arrangement of the light emitting elements 110 correspond to the arrangement of a probe (or probe fixing region), as will be described later. The light emitting elements 110 can emit light individually or simultaneously all together.

As for the probe substrate 200, as shown in FIG. 1, DNA probe molecules (pieces of DNA) 210, as a probe, are being fixed to each of a plurality of probe fixing regions 202 arranged on one face (upper face) of a transparent substrate 201, such as glass and plastic. The probe fixing region or the region 202 where the DNA probe molecules are fixed is formed in a range of 1 through 500 µm, preferably in a range of 10 through 100 µm. A plurality of methods of introducing DNA probe molecules are known. Specifically, on the probe fixing region 202, whose surface is made hydrophilic by a plasma surface processing or the like, or which is formed by vapor-depositing a gold thin film, self-assembled monolayer (SAM) having, for example, an amino group, a maleimide group, or the like at its terminal end is formed. The DNA probe can be bound to the probe fixing region 202 by covalent-bonding an amino group or a maleimide group or the like formed at this terminal end, and a succinic-acid ester group, a thiol group, or the like which is modified to the terminal end of the DNA probe molecules.

The optical filter 300 transmits the light with the wavelength of the fluorescence, the fluorescence being generated of pigment molecules intercalated in the DNA probe having a double helix structure that is made by the later-described hybridization reaction, and attenuates the light (emitted light from the light emitting element 110) with other wavelengths. In addition, the biological sample to which fluorochrome is added in advance may be bound (hybridization) to the probe.

As for the light receiving element substrate 400, a plurality of light receiving elements 410 are arranged on one face (opposite side of the probe substrate 200) of an insulating substrate 401. The light receiving element 410 is formed by charge coupled device (CCD), photo-diode (PD), a phototransistor, or the like. The light receiving element 410 measures the intensity of the fluorescence of each probe molecular layer 210 which transmits through the filter 300.

Figure 2:
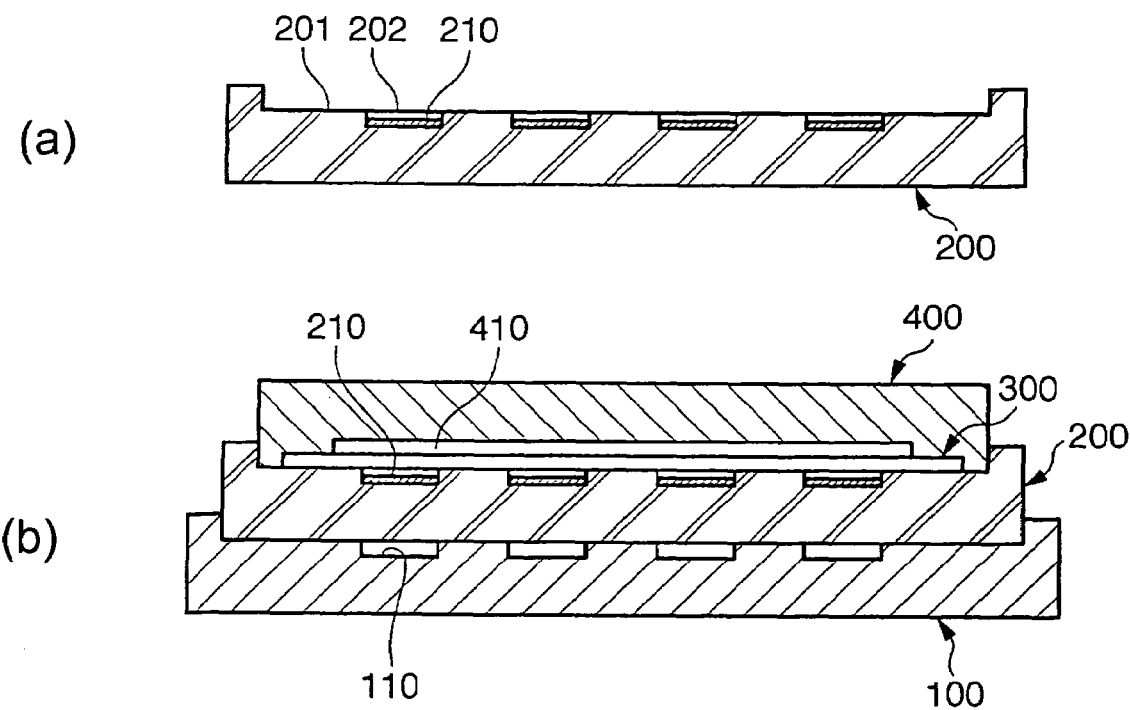
FIGS. 2(a) and 2(b) are an explanatory view explaining an example of constituting a biosensor by depositing substrates.

FIG. 2 shows a first exemplary embodiment using the biosensor as the substrate shown in FIG. 1, and in this figure, portions corresponding to the ones of FIG. 1 are given the same numerals and the description of such portion is omitted.

As shown in FIG. 2(*a*), the hybridization reaction is generated by spotting the sample to the probe fixing region 202 in the probe substrate 200. Namely, on the DNA probe molecular film 210 fixed to the probe fixing region 202, hybridization to the DNA probe molecules is generated by drop-discharging (ink-jet) a very small amount of solution of a complementary target DNA and a non-complementary DNA (biological sample) containing fluorochrome, or by discharge-supplying on a number of probe fixing regions 210 that is formed in an array form in the substrate 201 by a micro-spotter, or the like. The DNA probe molecules react with the complementary DNA to constitute a double helix structured DNA. Pigment molecules are inserted (intercalated) in this double helix portion. Since the DNA probe molecules do not react with the non-complementary DNA and do not constitute the double helix DNA, the pigment is not inserted. After carrying out the hybridization, samples which do not constitute the double helix with (which is not bound to) the DNA probe will be washed.

Then, as shown in FIG. 2(*b*), while aligning each element 110, 410, and the probe fixing region 202, the light emitting element substrate 100, the probe substrate 200, the filter 300, and the light receiving element substrate 400 are combined. The filter 300 and the light receiving element substrate 400 are not in contact with the probe 210.

Next, the light emitting element 110 in the light emitting element substrate 100 is made to emit light, and the fluorochrome of the probe 210 which constitutes the double helix with the sample is excited to generate fluorescence. This fluorescence is selected by the optical filter 300, and observed with the light receiving element 410 (for example, high sensitive CCD). The emitted light from the light emitting element 110 is shielded by the optical filter 300. When observing the fluorescence light, it is possible to avoid the influence of the adjacent light by operating one light emitting element within the region on which the leakage light has an influence, by making a plurality of light emitting elements 110 to emit light in time division manner. As will be described later, in cases that a light shielding layer is provided between the detecting regions of the units, and that there is little influence from mutual leakage lights, a plurality of light emitting elements can be operated. The intensity of the fluorescence generated from each probe 210 is observed with the light receiving element 410.

Thus, the presence of the hybridization reaction can be detected with high sensitivity by arranging the light receiving element close to the probe. The detected output from each light receiving element is data-processed by computer. Moreover, since each element is constituted by a thin substrate, the whole biosensor (detecting portion) is miniaturized. Moreover, according to the structure of the present embodiment, there is an advantage in that the light emitting element substrate 100, the filter 300, and the light receiving element substrate 400 can be used repeatedly.

Figure 3:
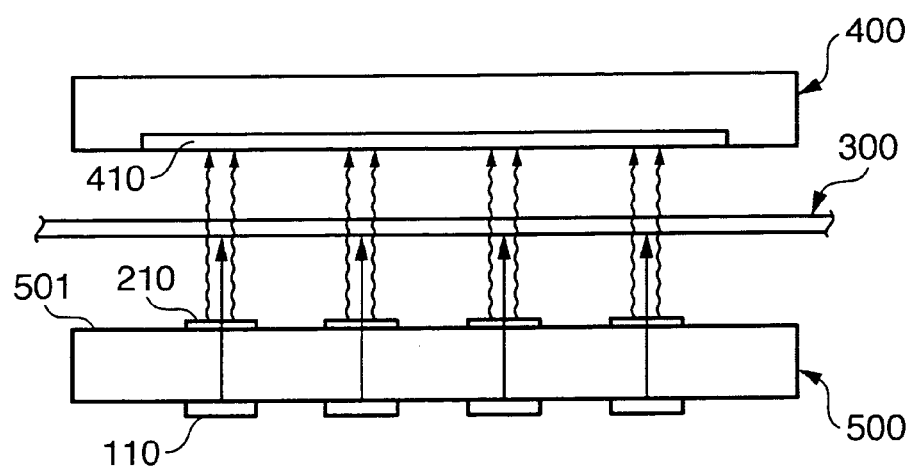
FIG. 3 is an explanatory view explaining an example of forming light sources and probes on two sides of one substrate.

FIG. 3 shows a second exemplary embodiment in which the light emitting element and the DNA probe are arranged in one substrate. In this figure, portions corresponding to the ones of FIG. 1 are given the same numerals and the description of such portion is omitted.

In this exemplary embodiment, the light emitting element substrate 100 and the probe substrate 200 shown in FIG. 1 are combined in one composite substrate 500. That is, for example, a plurality of light emitting elements 110 are arranged on one face (lower face) of a light transmissive insulating substrates 501, such as glass and plastic. As described above, as for the light emitting element 110, VCSEL, LED, an organic EL, or the like can be used.

Figure 11:
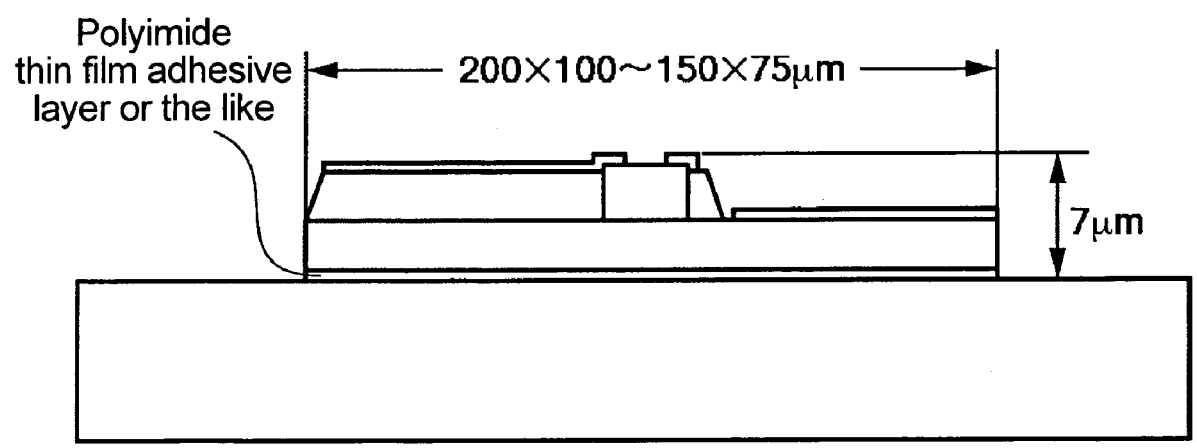
FIG. 11 is an explanatory view explaining an example of a thin film light emitting element (VCSEL) and light receiving element that is transferred to a glass substrate.

FIG. 11 shows an example of providing the VCSEL in the substrate.

A DNA probe 210 is arranged in a plurality of probe fixing regions on the other face (upper face) of the substrate 501. In addition, in FIG. 3, the probe 210 is formed as to protrude from the surface of the substrate 501, however, the probe 210 may be formed in a concave portion like the case of FIG. 1.

Such a structure can be obtained, after carrying out lyophilic processing to one face (upper face) of the substrate 501 by plasma, by transferring the light emitting element 110 chip to the other face (lower face) of the substrate 501, as will be described later (refer to FIG. 13), and furthermore, by fixing the DNA probe to the probe fixing region.

If a light source and the probe substrate 500 which integrates this light emitting element 110 and the probe 210 is used, either one of the substrate 100 or 200 can be reduced in the above-described structures shown in FIGS. 1 and 2. Moreover, the biosensor can be miniaturized by that amount.

Figure 4:
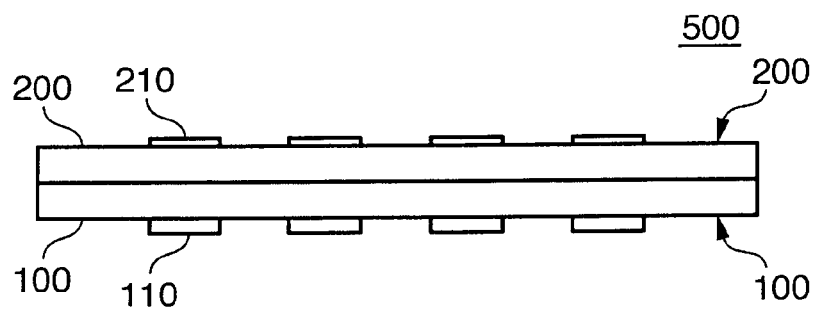
FIG. 4 is an explanatory view explaining an example of forming the substrate of FIG. 3 by bonding.

FIG. 4 shows a third exemplary embodiment in which the light source and the probe substrate 500 shown in the second exemplary embodiment is formed bonding two substrates 100 and 200. If making such a structure, there is an advantage in that the light emitting element substrate 100 and the probe substrate can be manufactured separately by different manufacturing methods (or manufacturing processes) or under different process conditions.

Figure 5:
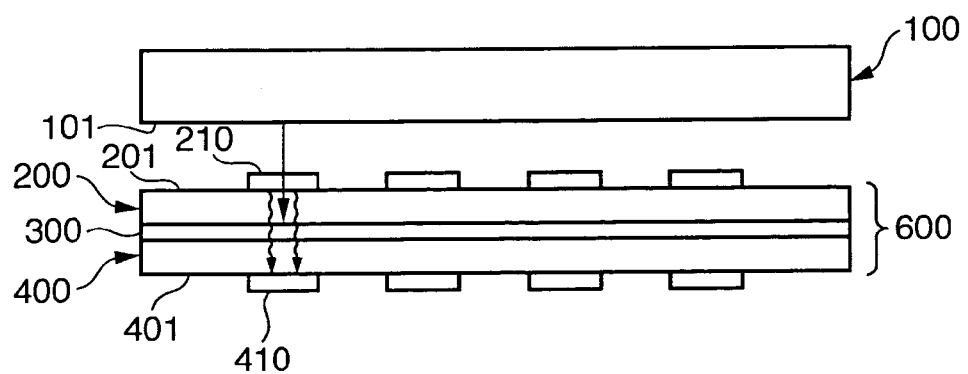
FIG. 5 is an explanatory view explaining an example of forming a filter in between substrates.

FIG. 5 shows a fourth exemplary embodiment in which the light receiving element and the DNA probe are arranged in one substrate. In this figure, portions corresponding to the ones of FIG. 1 are given the same numerals and the description of such portion is omitted.

In the embodiment, the probe substrate 200, the filter 300, and the light receiving element substrate 400 shown in FIG. 1 are combined as one light receiving and the probe substrate 600. In other words, a plurality of light receiving elements 410 are arranged on one face (lower face) of a light transmissive insulating substrate 401, such as glass and plastic. As described above, as for the light receiving element 410, PD, CCD, a photo-transistor, or the like can be used. In a plurality of probe fixing regions on one face (upper face) of the light transmissive substrate 201 in the probe substrate 200, the DNA probe 210 is arranged. In addition, in FIG. 5, the probe 210 is formed as to protrude from the surface of the substrate 201, however, the probe 210 may be formed in a concave portion like the case of FIG. 1. The filter 300 is arranged between the probe substrate 200 and the light receiving substrate 400, the light receiving and the probe substrate (composite substrate) 600 is formed by depositing the probe substrate 200, the filter 300, and the light receiving element substrate 400.

Such a structure, for example, obtains the probe substrate 200 by carrying out the lyophilic processing to one face (upper face of the figure) of the glass substrate 201 by plasma. The light receiving element substrate 400 is formed transferring the light receiving element 410 chip to one face (lower face of the figure) of the glass substrate 401 (refer to FIG. 13). The filter 300 can be constituted by gelatin film mixed with pigment, a color glass, a diffraction grating, or the like. The light receiving and probe substrate 600 is obtained by bonding the probe substrate 200, the filter 300, and the light receiving element substrate 400. Furthermore, this structure is completed by fixing the DNA probe to the probe fixing region in the substrate 201 of the light receiving and probe substrate 600.

The hybridization reaction is generated by spotting the biological sample to each probe in the light receiving and probe substrate 600 that is constituted this way. The DNA probe molecules react with the complementary DNA to constitute a double helix structured DNA. Pigment molecules are inserted in this double helix portion.

After carrying out the hybridization, samples which do not constitute the double helix with the DNA probe (which are not bonded) will be washed off. Excitation light is applied by the light emitting element substrate 100 from the above of this substrate 600, and the presence of the fluorescence of each probe 210 is observed by the light receiving element 410.

If the light receiving and probe substrate 600 which integrates this light receiving element 410 and the probe 210 is used, either one of the substrate 200 or 400 can be reduced in the above-described structures shown in FIGS. 1 and 2. Moreover, the biosensor can be miniaturized by that amount.

Figure 6A:
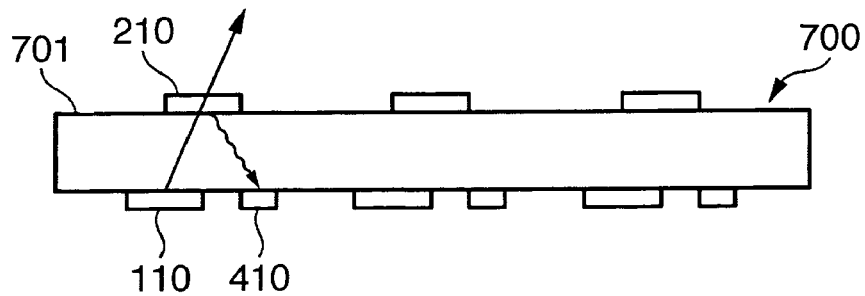
FIG. 6(a) is an explanatory view explaining an example of forming light emitting elements and light receiving elements on one face of a substrate, and forming probes on the other face.

FIGS. 6(a) and (b) show a fifth exemplary embodiment in which the light emitting element, the probe, and the light receiving element are formed in one substrate. In this figure, portions corresponding to the ones of FIG. 1 are given the same numerals and the description of such portion is omitted.

In exemplary embodiment, the probe 210 is fixed to a plurality of probe fixing regions on one face (upper face) side of a light transmissive substrates 701, such as glass and plastic, and the light emitting element 110 and the light receiving element 410 are arranged on the other face (lower face) of a substrate 701. The light emitting element 110 excites the fluorochrome which is intercalated in the probe 210 by hybridization reaction. The light receiving element 410 observes the emission of the fluorochrome, and outputs a light receiving level signal which judges the presence of the binding of the complementary DNA.

In addition, in case that the output light of the light emitting element 110 reflects in the probe fixing region and does not return to the light receiving element 410, the light filter 300, which attenuates the output of the light emitting element 110 and selectively transmits the fluorescence of the fluorochrome, is not necessary. However, in case that a part of the output light of the light emitting element 110 is incident upon the light receiving element 410, the filter 300 can be arranged between the substrate 701 and the light receiving element 410. Moreover, in place of the arrangement of the filter 300, the light receiving element 410 having a wavelength selectivity, the sensitivity being high to the wavelength of the fluorescence light of the fluorochrome and low to the wavelength of the output light of the light emitting element 110 may be used.

Figure 6B:
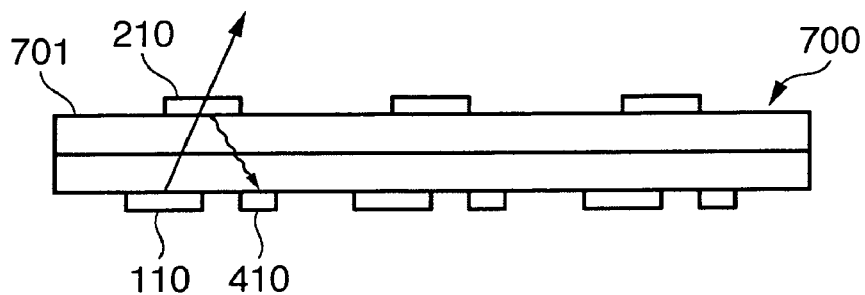
FIG. 6(b) is an explanatory view explaining an example of forming a substrate by bonding.

Also in this exemplary embodiment, as shown in FIG. 6(b), the substrate 701 can be formed by bonding. In this way, there is an advantage in that the light emitting element and light receiving element substrate and the probe substrate can be manufactured separately by different manufacturing processes or under different process conditions.

Figure 7A:
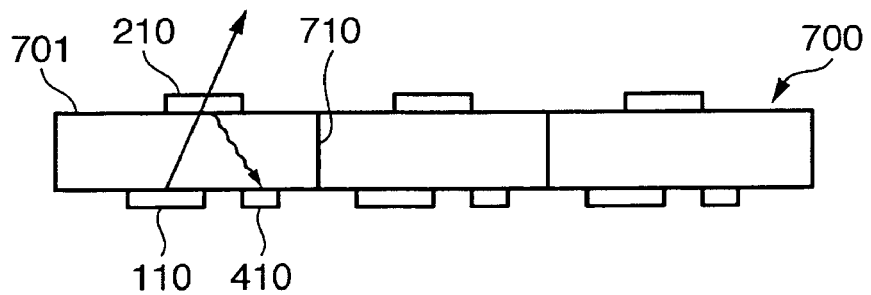
FIG. 7 is an explanatory view explaining an example of forming furthermore light shielding regions in the structure of FIG. 6.

FIGS. 7(a) and (b) shows a sixth exemplary embodiment. In this figure, portions corresponding to the ones of FIG. 6 are given the same numerals.

As shown in FIG. 7(a), in this exemplary embodiment, in the structure having the light emitting element 110, the probe 210, and the light receiving element 410 provided in one substrate 701, a light shielding layer 710 is arranged between unit sensor regions comprising the light emitting element 110, the probe 210, and the light receiving element 410. The leakage of the output light of the light emitting element 110 into the adjacent regions and the leakage of the fluorescence from the fluorochrome of the probe 210 into the adjacent regions can be prevented by the light shielding layer 710. The light shielding layer 710 is formed, for example, by discharging black resin from a drop-discharging head (ink-jet method) to the groove that is formed in the substrate 701 by dicing or etching.

According to such a structure, in case that the light leakage is a problem in the structure shown in the fifth exemplary embodiment (refer to FIG. 6), this problem can be eliminated.

Figure 7B:
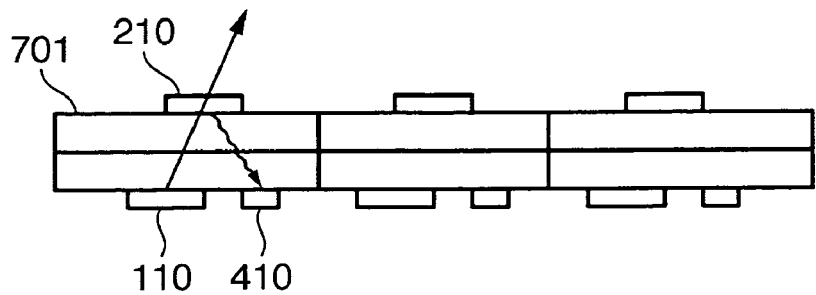

FIG. 7(b) shows, furthermore, an example of constituting the substrate 701 by depositing (bonding) two substrates. In this way, there is an advantage in that the light emitting element and light receiving element substrate, and the probe substrate can be manufactured separately by different manufacturing processes or under different process conditions.

Figure 8A:
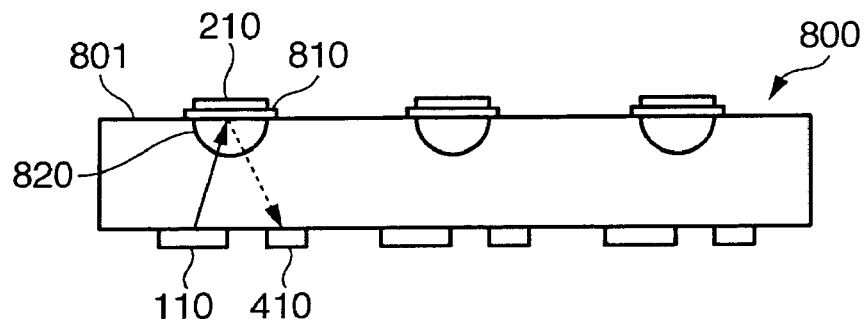
FIG. 8 is an explanatory view explaining an example of forming a biosensor which carries out measurement by the surface plasmon resonance (SPR) method on one substrate.

FIGS. 8(a) and (b) show a seventh exemplary embodiment in which the presence of the hybridization reaction of the biological sample to the DNA probe is distinguished by the surface plasmon resonance (SPR) method.

In this figure, portions corresponding to the ones of FIG. 1 are given the same numerals and the description of such portion is omitted.

In this exemplary embodiment, as shown in FIG. 8(a), in a plurality of probe fixing regions on one face (upper face) of the light transmissive substrate 801, such as glass and plastic, a metal thin film 810 is formed by a sputtering method, a vapor-depositing method, or the like. Preferably, an approximately 500 angstrom gold (Au) thin film 810 is used. The DNA probe 210 modified by thiol is fixed on this gold thin film 810. Under (back face of) the gold thin film 810, a prism with the refractive index of approximately 1.50 to 1.80 is formed by a microlens 820.

The light emitting element 110 and the light receiving element 410 are arranged on the other face (lower face) of the substrate 801. As for the light emitting element 110 that excites plasma, for example, VCSEL, an organic EL dot, or the like whose output beam is narrowed with a microlens, can be used. As for the light receiving element 410, Photo-Diode, CCD, or the like can be used. The excitation light outputted from the light emitting element 110 is reflected on the gold surface 810 through the microprism 820. The reflected light is incident upon the light receiving element 410 through the microprism 820. When the hybridization reaction of the DNA probe molecules is generated on the surface of the gold thin film, the refractive index on the gold thin film will change greatly. The change in a surface-plasmon-resonance angle is detected by the light receiving element. When the hybridization reaction is not generated, the change in the surface-plasmon-resonance angle is not generated. Accordingly, the reaction in each probe fixing region can be observed in a short time.

Figure 8B:
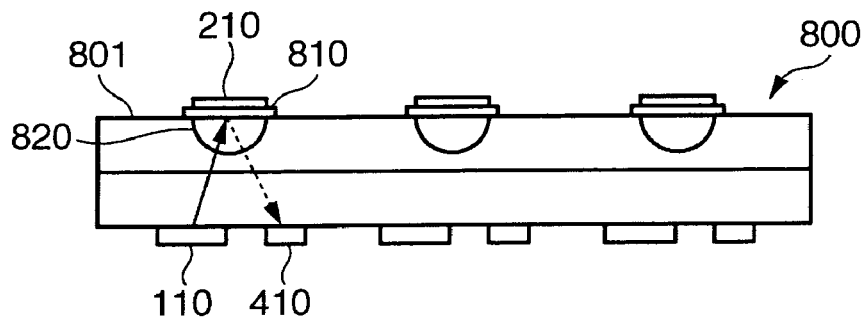

FIG. 8(b) shows, furthermore, an example of constituting the substrate 801 by depositing (bonding) two substrates. In this way, there is an advantage in that the light emitting element and light receiving element substrate and the probe substrate, in which the microprism is formed, can be manufactured separately by different manufacturing processes or under different process conditions.

Figure 9A:
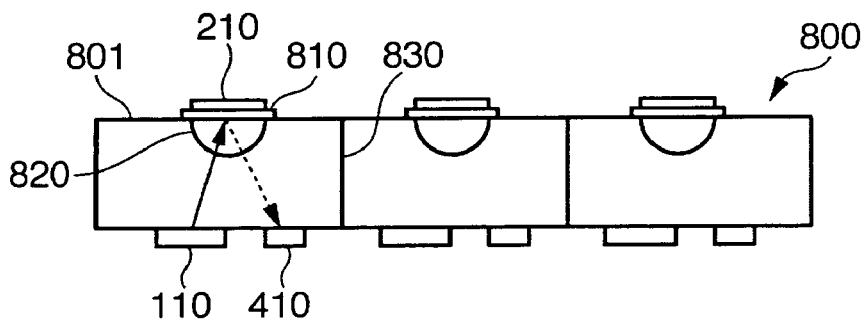
FIG. 9 is an explanatory view explaining an example of forming furthermore light shielding regions in the structure of FIG. 8.
Figure 9B:
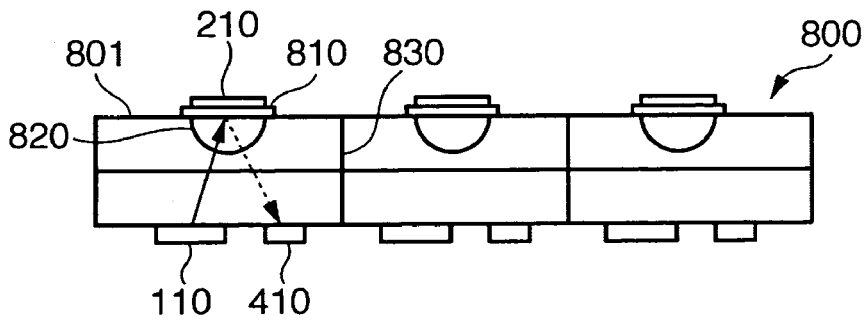
Figure 10:
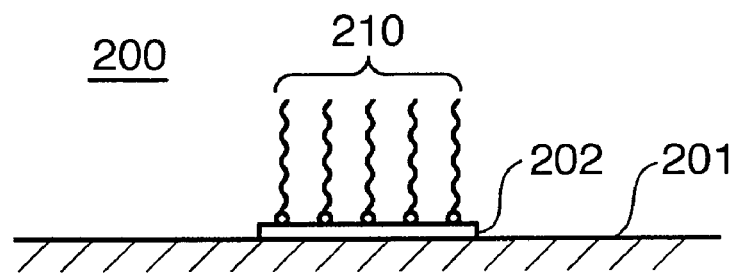
FIG. 10 is an explanatory view explaining a probe comprising pieces of DNA.

FIG. 9 shows an eighth exemplary embodiment. In this figure, portions corresponding to the ones of FIG. 8 are given the same numerals and the description of such portion is omitted. In this example (FIGS. 9(a) and (b)), each region between the unit sensor regions is shielded from light by the light shielding layer 830. Accordingly, the leakage light from the light emitting elements of the adjacent sensors and the leakage light due to the reflected light in the substrate can be shielded, and each unit sensor can be operated simultaneously.

Next, the manufacturing process of the biosensor will be described. In the above-described biosensor substrate, the light emitting element and the light receiving element are arranged. In this embodiment, the arrangement of this light emitting element or the like to the substrate is carried out by a "transfer technology".

FIG. 11 shows an example of transferring a light emitting element (VCSEL) chip on a glass substrate. The light emitting element is fixed to a glass substrate or a plastic substrate through a thin film adhesive layer, such as polyimide resin or epoxy resin.

Figure 12:
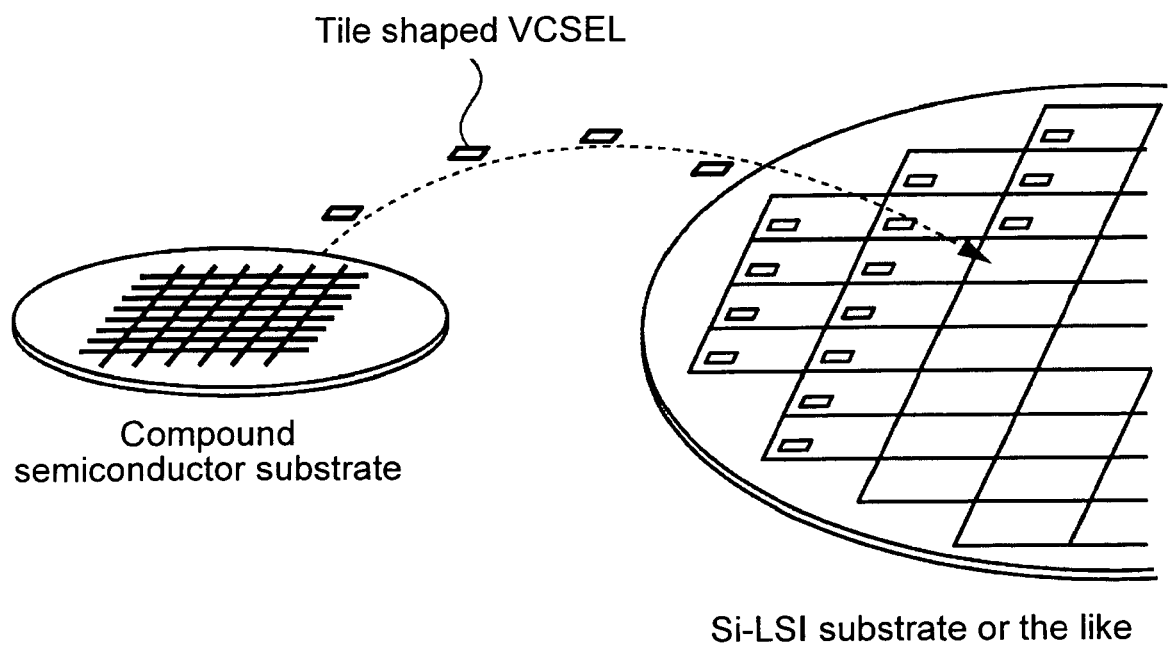
FIG. 12 is a conceptual view explaining the transfer of a compound semiconductor device (VCSEL, LED, photo-transistor, or the like) manufactured in a compound semiconductor substrate to the other substrate.

FIG. 12 is an explanatory view explaining the transfer technology conceptually, in which chips of a light emitting element or light receiving elements (VCSEL, LED, PD (photo-diode), PTr (photo-transistor), or the like) formed in a compound semiconductor substrate, such as a gallium arsenide substrate, are peeled off from the compound semiconductor substrate and bonded (transferred) to a glass substrate, a plastic substrate, a silicone substrate, or the like. The glass substrate, the silicone substrate, or the like may be a glass TFT substrate, a silicone LSI substrate, or the like. As for the peel-transfer, epitaxial lift-off technology (ELO) which enables a chip to be peeled off by etching the inter layer of the chip can be used.

With reference to FIG. 13, the manufacturing process of the biosensor using the transfer technology will be described. First, a plurality of elements (light emitting elements, light receiving elements) are formed in a gallium arsenide substrate 10. The light emitting element 110 is formed in the example shown in the figure. At this time, an aluminum arsenic (AlAs) layer is formed, as the inter layer 20, in the lower layer of the light emitting element 110. After forming the light emitting element 110, grooves are cut, in a grid pattern, halfway in the gallium arsenide substrate 10 by dicing (FIG. 13(a)).

Wet etching is carried out in a lateral direction from these grooves, and the inter layer 20 is removed to a level in which the light emitting element chip 110 can be peeled off. An inter transfer film 30 on whose surface is applied with adhesive is bonded to the light emitting element 110 (FIG. 13(b)). Each light emitting element 110 is peeled off from the gallium arsenide substrate 10 by lifting off the inter transfer film 30, and moved, as an element chip, to the inter transfer film 30 side (FIG. 13(c)).

Next, alignment is performed as to transfer the light emitting element chip 110, which moved to the inter transfer film 30, to a predetermined position in the glass substrate 101. Adhesive 103 is thinly applied to the predetermined position in the glass substrate 101, in advance (FIG. 13(d)). A stamper 40 is pushed down from behind (from above) the inter transfer film 30, and the light emitting element chip 110 is stuck closely to the glass substrate 101 to be fixed.

On this occasion, the adhesive 103 applied on the glass substrate 101 can be made thermosetting (or photo-setting) and the adhesive of the inter transfer film 30 can be made thermosoftening (or photo-softening).

The light emitting element chip 110 can be attached to the glass substrate 101 by providing the stamper 40 with a heater (not shown) and heating up to a suitable temperature. When the adhesive is made photo-setting, irradiation of ultraviolet rays or the like is carried out. Moreover, the peeling off from the inter transfer film 30 may be facilitated by laser ablation (FIG. 13(e)).

Next, the light emitting element chip 110 is moved to the substrate 101 from the inter transfer film 30 by lifting off the inter transfer film 30 (FIG. 13(f)).

Thus, the transfer of the light emitting element 110 to the predetermined position in the glass substrate 101 is carried out.

Figure 14:
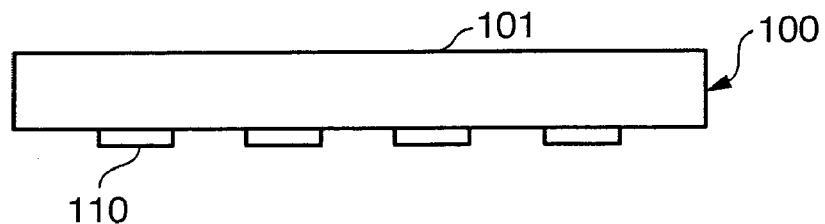
FIG. 14 is an explanatory view explaining a substrate manufactured by ELO process.

As for the light receiving element chip 410 formed in the compound semiconductor substrate, the transfer to the glass substrate can be carried out in the same manner. Thus, the element chip 110 can be "transferred" to the glass substrate or the plastic substrate 101 (FIG. 14). On the face (upper face shown in the figure) of the above-described glass substrate 101 in which the probe is formed, lyophilic processing such as plasma processing is carried out, in advance, to a part of or the whole of the upper face of the substrate to form a plurality of probe fixing regions, and furthermore the DNA probe is fixed to the probe fixing region after the transfer of the light emitting element chip and the light receiving element chip.

In addition, the transferred element chip may be the light emitting element 110 or the light receiving element 410. A composite substrate constituting a biosensor by one substrate, as shown in FIG. 6, is obtained by transferring the light emitting element 110 and the light receiving element 410 to one substrate.

Figure 15A:
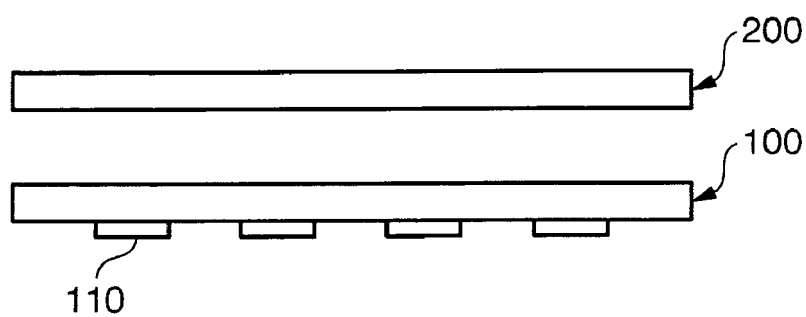
FIG. 15 is a process flowchart explaining the process of bonding two substrates.
Figure 15B:
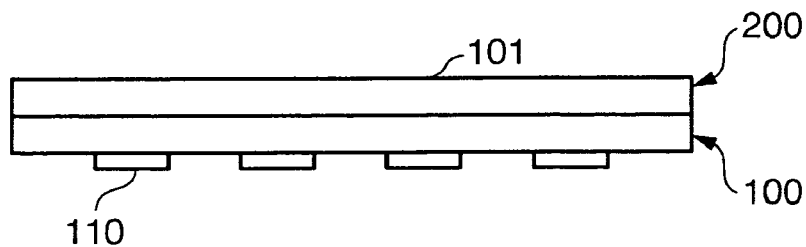

FIG. 15 is a figure explaining an example of forming a composite substrate by bonding two substrates. As shown in FIG. 15(a), the plasma processed substrate 200 and the above-described substrate 100 to which the light emitting element 110 is transferred are prepared. Next, both substrates are bonded together through adhesive, as shown in FIG. 15(b). Furthermore, the DNA probe molecules are fixed to the upper face of the lyophilic processed substrate 200 to form the probe 210 (refer to FIG. 4). Accordingly, the multi layered substrate shown in FIG. 4 can be obtained. Thus, a biosensor can be also manufactured by bonding substrates.

While this invention has been described in conjunction with the specific embodiments thereof, it is evident that many alternatives, modifications, and variations will be apparent to those skilled in the art. Accordingly, preferred embodiments of the invention as set forth herein are intended to be illustrative, not limiting. There are changes that may be made without departing from the spirit and scope of the invention.

What is claimed is:

1. A biosensor, comprising:
   a light transmissive substrate having a first face and a second face opposing the first face;
   a probe fixing region to which a probe is fixed, the probe fixing region provided on the first face of the light transmissive substrate;
   a light emitting element provided on the second face of the light transmissive substrate that irradiates the probe fixing region; and
   a light receiving element provided on the second face of the light transmissive substrate that detects light intensity of reflected light from the probe fixing region.

* * * * *